United States Patent [19]

Kelman

[11] 4,451,938

[45] Jun. 5, 1984

[54] INTRAOCULAR LENS AND METHOD OF POSITIONING THE SAME IN AN EYE

[76] Inventor: Charles D. Kelman, Floral Park, N.Y.

[21] Appl. No.: 422,374

[22] Filed: Sep. 24, 1982

[51] Int. Cl.³ .............................. A61F 1/16; A61F 1/24
[52] U.S. Cl. ............................................................ 3/13
[58] Field of Search ........................................ 3/13, 1

[56] References Cited

U.S. PATENT DOCUMENTS

| | | | |
|---|---|---|---|
| 4,056,855 | 11/1977 | Kelman | 3/13 |
| 4,092,743 | 6/1978 | Kelman | 3/13 |
| 4,174,543 | 11/1979 | Kelman | 3/13 |
| 4,268,921 | 5/1981 | Kelman | 3/13 |
| 4,370,760 | 2/1983 | Kelman | 3/13 |

Primary Examiner—Ronald L. Frinks
Attorney, Agent, or Firm—Charles A. Blank; Henry Sternberg

[57] ABSTRACT

An intraocular lens and method of positioning the same in a human eye in which the lens has, for example, two body portions which are separable outside the eye and two position-fixation members extending therefrom. The individual lens body portions and position-fixation members can be snaked into the eye through a smaller opening in the eye than the diameter of the lens body and the individual lens portions are connected together inside the eye by the surgeon to form the lens which is then positioned and seated in the eye by the surgeon.

23 Claims, 12 Drawing Figures

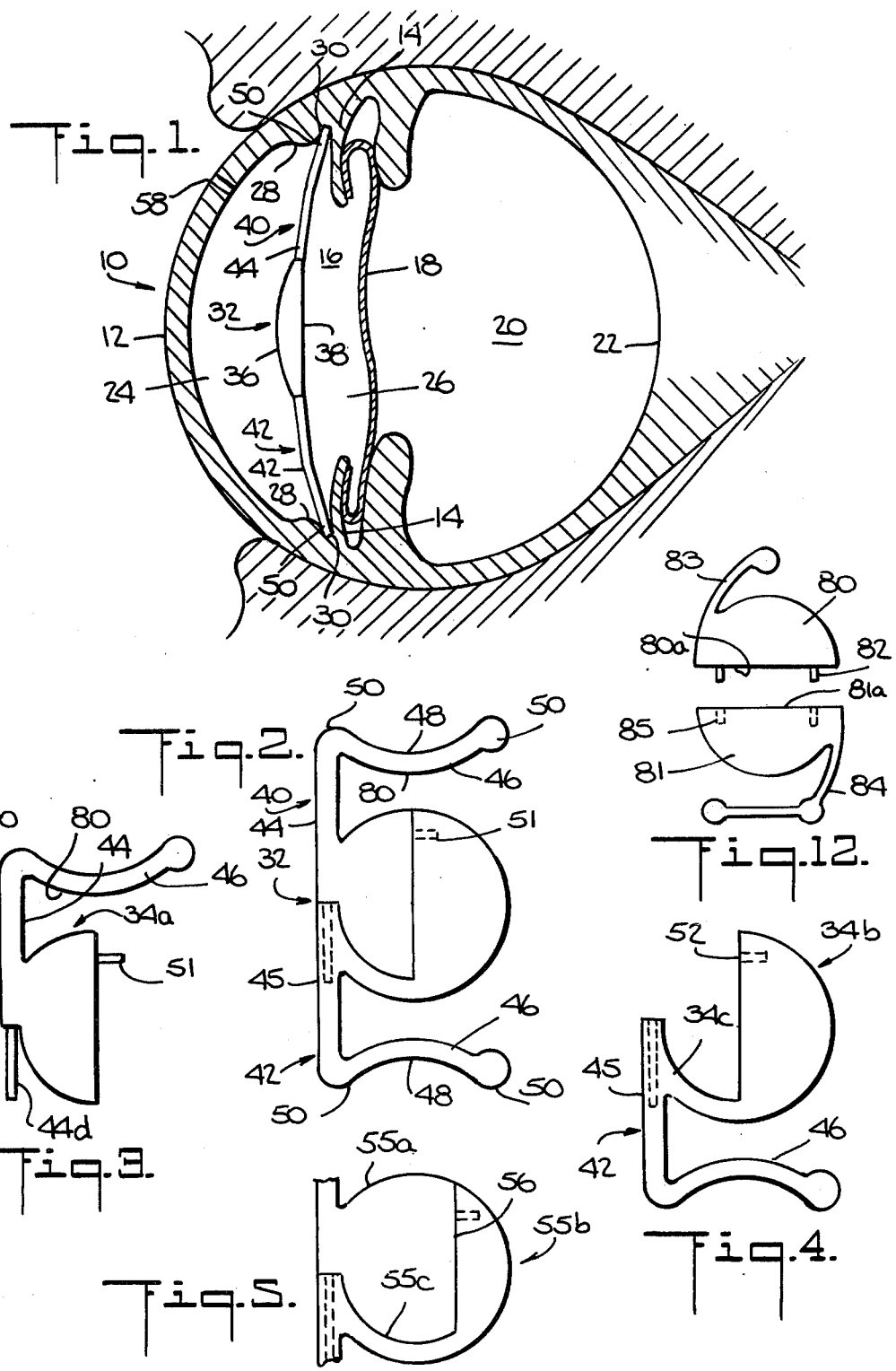

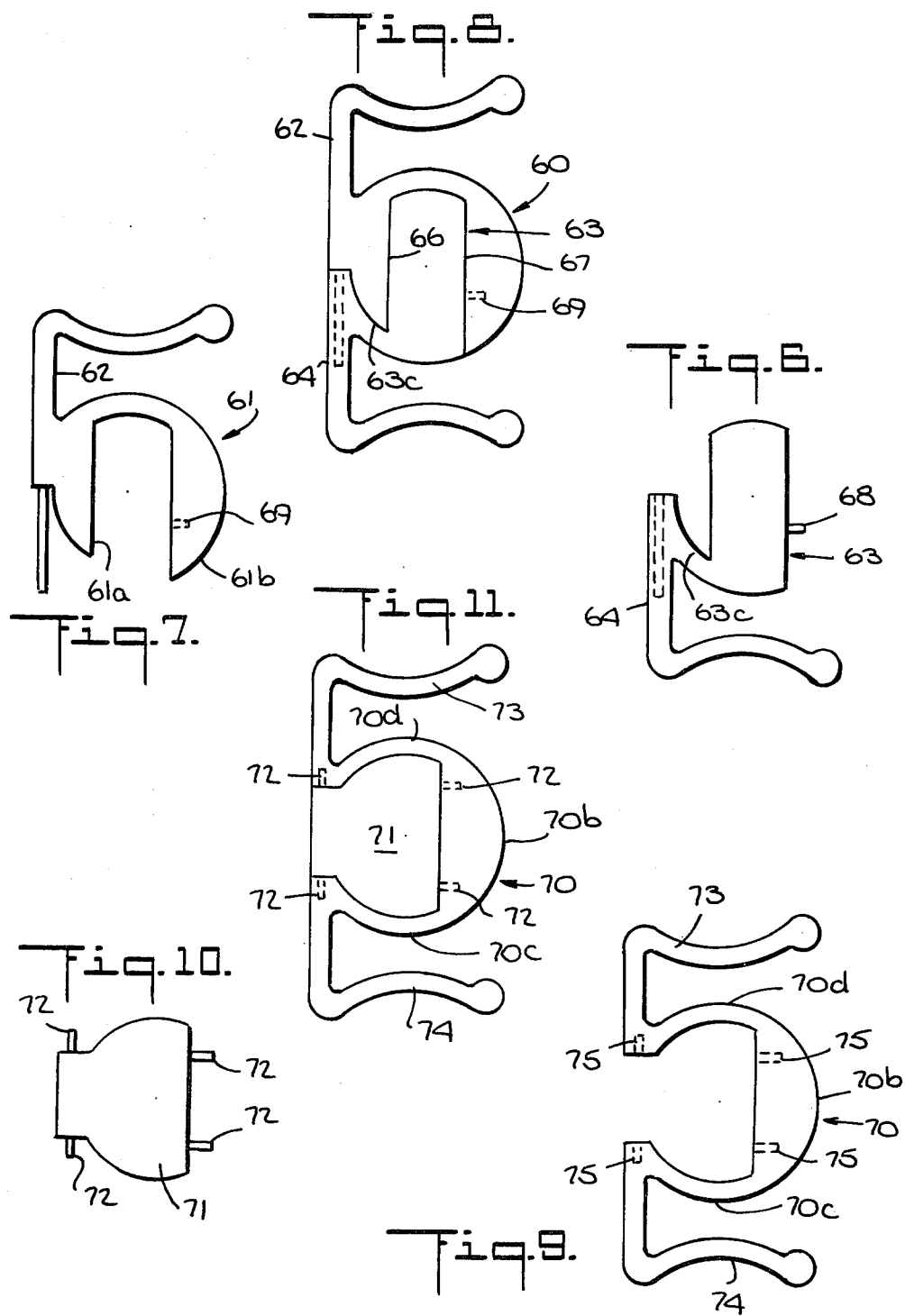

INTRAOCULAR LENS AND METHOD OF POSITIONING THE SAME IN AN EYE

This invention relates to intraocular lenses for the human eye, and, more particularly, to intraocular lenses of the type which can be positioned in the anterior chamber, the posterior chamber, or partially in the anterior chamber and partially in the posterior chamber of the eye. The invention also relates to methods of positioning such lenses in an eye.

One type of intraocular lens is described and claimed in my U.S. Pat. No. 4,174,543 issued Nov. 20, 1979. Such a lens is inserted into the eye through a corneo-scleral incision that may be also used to remove the natural lens. To minimize the possibility of injury to the eye, it is important that the incision be made as small as possible. To this end, another type of lens is described and claimed in my co-pending application Ser. No. 393,057 filed June 28, 1982, entitled Intraocular Lens And Method of Inserting An Intraocular Lens Into An Eye. In my co-pending application a deformable lens is described and claimed which allows the surgeon to make an incision in the eye which is smaller than the diameter of the lens body or optic of the lens.

It is an object of the present invention, therefore, to provide a new and improved intraocular lens which avoids one or more of the limitations of prior such lenses.

It is another object of the invention to provide a new and improved intraocular lens which can be inserted into the eye through an opening which is smaller than the diameter of the lens body or optic.

It is another object of the invention to provide a new and improved method of positioning an intraocular lens in an eye, which avoids one or more of the limitatiions of prior such methods.

It is another object of the invention to provide a new and improved method of positioning an intraocular lens in an eye utilizing a smaller opening in the eye than the diameter of the lens body for insertion of the lens into the eye.

In accordance with the invention, an intraocular lens comprises a lens body having a plurality of portions which are separable outside an eye. The lens also includes a plurality of position-fixation members extending from the lens body for fixating the position of the lens body portions within the eye. A plurality of lens portions comprise the lens body portions and the position-fixation members. The plurality of lens portions are individually insertable through an opening in the eye and are connectable within the eye to form the lens.

Also in accordance with the invention, a method of positioning in an eye an intraocular lens having a plurality of lens portions which are separable outside the eye, the lens portions including lens body portions and position-fixation members, the lens portions being connectable, comprises inserting a first lens body portion and at least one position-fixation member through an opening in the eye. The method also includes inserting a second lens body portion through the opening in the eye to position the lens body portions and the position-fixation members in the eye.

For a better understanding of the present invention, together with other and further objects thereof, reference is made to the following description, taken in connection with the accompanying drawings, and its scope will be pointed out in the appended claims.

Referring now to the drawings:

FIG. 1 is a simplified schematic sectional view of an eyeball implanted with an intraocular lens embodying a preferred form of the present invention;

FIG. 2 is a plan view of the intraocular lens represented in FIG. 1;

FIG. 3 is a plan view of one portion of the lens of FIGS. 1 and 2;

FIG. 4 is a plan view of another portion of the lens of FIGS. 1 and 2;

FIG. 5 is a plan view of a lens body or optic which may be utilized in lieu of the lens body or optic of the lens of FIGS. 1 and 2;

FIG. 6 is a plan view of a lens portion of another embodiment of a lens constructed in accordance with the invention;

FIG. 7 is a plan view of another lens portion cooperative with the lens portion of FIG. 6 to form another embodiment of a lens constructed in accordance with the invention;

FIG. 8 is a plan view of a lens constructed in accordance with the invention having the portions represented in FIGS. 6 and 7;

FIG. 9 is a plan view of a lens portion of another embodiment of a lens constructed in accordance with the invention;

FIG. 10 is plan view of another lens portion cooperative with the lens portions of FIG. 9 to form another embodiment of a lens constructed in accordance with the invention; and FIG. 11 is a plan view of a lens constructed in accordance with the invention having the portions represented in FIGS. 9 and 10.

FIG. 12 is a plan view of a pair of lens portions shown in spaced apart condition prior to assembly thereof into a lens constructed in accordance with the invention.

Referring now more particularly to FIGS. 1 and 2 of the drawings, reference numeral 10 generally designates an eyeball as shown in simplified schematic cross-section in FIG. 1. Portions of the eyeball structure which are not believed to be essential to an understanding of the invention have been omitted for the sake of clarity.

The eyeball 10 includes a cornea 12, a diaphragm of iris 14 having a central opening or pupil 16, a membrane 18, vitreous humor 20 and a retina 22. The natural lens, which normally occupies part of the region between the membrane 18 and the iris 14, has been omitted since the invention deals with artificial substitutes for a natural lens. An aqueous zone, between the cornea 12 and the membrane 18, is subdivided by the iris 14 into an anterior chamber 24 and a posterior chamber 26. A scleral spur 28 in the anterior chamber 24 is spaced from the iris 14 thereby defining a groove 30.

An intraocular artificial lens for the eyeball 10 is generally indicated by reference numeral 32 in FIG. 1 and will first be described generally with reference to FIGS. 1 and 2. The lens 32 can be formed of any suitable material which is compatible with the environment of the eyeball, such as a non-toxic plastic, for example, polymethylmethacrylate.

The lens 32 includes a medial light-focusing lens body 34 or optic having, for example, a convex anterior surface 36 and a generally flat posterior surface 38. A pair of oppositely disposed symmetrical position-fixation members 40 and 42 include respective stem portions 44 and 45 that extend from the periphery of the lens body 34.

The stem portions 44 and 45 individually have identical limb portions 46, 46 joined thereto in cantilever arrangement. A concave outer seating edge 48 of each of the limb portions 46, 46 terminates with respective contact lobes 50, 50. With this arrangement an inner edge portion 80 of each limb portion 46 is free from contact with the periphery of the lens body 34.

Referring now more particularly to FIGS. 3 and 4 of the drawings, the intraocular lens 32 of FIG. 2 will be described in greater detail. The intraocular lens 32 comprises a lens body 34 having a plurality of portions 34a, 34b which are separable outside an eye. A curved lens body portion 34c extending from the lens body portion 34b may be a portion of the lens body portion 34b. A plurality of position-fixation members 40, 42 individually extend from the plurality of portions 34a, 34b of the lens body for fixating the position of the lens body portions within the eye. In this connection, the lens body portion 34c may alternatively be a portion of the position-fixation member 45. A plurality of lens portions comprise individual ones of the lens body portions 34a, 34b and individual ones of the position-fixation members 40, 42. The plurality of lens portions 34a, 40 and 34b, 42 are individually insertable through an opening in the eye and are connectable within the eye to form the lens 32.

From the foregoing description it will be seen that the plurality of portions of the lens body preferably is two portions 34a and 34b. The first lens body portion 34a has the first position-fixation member 40 extending tangentially therefrom to form a first lens portion. The second lens body portion 34b, including the portion 34c, has the position-fixation member 42 extending therefrom to form a second lens portion. The first and second position-fixation members 40, 42 are connectable within the eye. The first position-fixation member 40 has a longitudinally extending portion 44d and the second position-fixation member 42 has a hollow longitudinal extending portion 45. The longitudinal extending portion 44d is insertable into the hollow longitudinally extending portion 45 within the eye.

For example, when positioning the lens 32 in the anterior chamber, the surgeon can first snake through the incision or opening 58 the limb portion 46 attached to the hollow longitudinally extending portion 45 of the position fixation member 42. Then he can insert the hollow longitudinally extending portion 45 and thereafter snake through the opening the curved lens body portion 34c and the lens body portion 34b. The lens body portion 34b and the position-fixation member 42 can be positioned in the anterior chamber and maintained in position temporarily by another instrument inserted by the surgeon through another opening in the eye usually made for other purposes. The lens body portion 34a and the position-fixation member 40 may be inserted through the opening 58 in a similar manner. The longitudinally extending portion 44d of the position-fixation member 40 may be inserted by the surgeon into the hollow longitudinally extending portion 45 of the position-fixation member 42 within the eye until the lens body portion 34a is positioned against the lens body portions 34b, 34c. Thus, the length of the incision or opening 58 need only be long enough to insert a lens body portion having one half the diameter of the lens body portion 34 of FIG. 2. For example, the incision may be slightly over 2.5 mm long for insertion of a lens body having a diameter of 5 mm. The lens body portion 34 may, for example, have a thickness of 0.4 mm. For example, the thickness of the position-fixation member 40 can be 0.2 mm, the width thereof about 1.2 mm, and the length thereof including portion 44d about 10 mm. For example, the outer thickness dimension of the hollow portion 45 of position-fixation member 42 may be about 1.2 mm, the outer wider dimension thereof about 1.2 mm, and the length thereof about 7 mm. The distance between corresponding contact lobes 50, 50 from one of the members 40, 42 to the other may be, for example, about 14 mm. The radius of curvature of the concave outer seating edge 48 of each member 40, 42 may be, for example, approximately 180 mm.

The limb portions 46, 46 of the position-fixation members 40, 42 are slighly inclined and seat in the anterior chamber angle 30. The posterior surface 38 of the lens bodys 34 lies in a plane that is substantially coplanar with the plane of the stem portions 44, 45 and is spaced from the plane of the iris by about 0.25 mm to 0.75 mm. This spacing is desirable to maintain the lens body 34 out of contact with the iris and to prevent the lens from interfering with expansion and contraction of the pupil 16. Therefore, the limb portions 46, 46 are slightly inclined with respect to the posterior lens surface 38 and the stem portions 44, 45 as shown in FIG. 1.

The lens preferably includes means for locking together the first and second body portions 34a and 34b after insertion thereof into the eye. The means for locking together the first and second body portions 34a and 34b after insertion thereof into the eye may, for example, comprise a pin 51 extending from body portion 34a and an aperture 52 in body portion 34b into which the pin 51 is inserted. By bending the second body portion 34b clockwise away from the stem portion 45 after portion 44d has been initially inserted in stem 45, such bending being allowed by the flexible nature of curved lens body portion 34c, insertion of the pin 51 into aperture 52 is facilitated.

The lens body 32 has a circular periphery and the first and second lens portions 34a, 40 and 34b, 34c, 42 can be so connected within the eye so that the first and second lens body portions abut each other along a diameter of the lens body. The connected lens body portions 34a and 34b, 34c and the connected position-fixation members 40, 42 may then be positioned and seated within the eye by the surgeon.

Referring to FIG. 5, a lens body 55 which can be utilized in lieu of the lens body portions 34a, 34b, 34 c is represented. The lens body 55 of FIG. 5 has a circular periphery and the position-fixation members attached thereto (not shown in FIG. 5) can be so connected within the eye so that the first and second lens body portions 55a and 55b, including portion 55c, abut each other along a line displaced from a diameter of the lens body. Thus, the lens body portion 55a may have a maximum width of, for example, 3 mm between its periphery and the straight edge along line 56 of abutting lens body portion 55b. The lens body portion 55b may have a maximum width of, for example, 2 mm between its periphery and the straight edge along line 56 of abutting lens body portion 55a. An incision in the eye of only slightly more than 3 mm is necessary to insert the 3 mm portion 55a thorugh the opening in the eye. However, the lens body portion 55 has the advantage that the abutting edges of lens portions 55a, 55b which abut each other along line 56 are displaced from the central focal region of the lens, thereby minimizing any interference in the primary region of vision.

Referring now to FIGS. 6, 7 and 8, the lens 60 of FIG. 8 may be of similar construction to the lens 32 of FIGS. 1 and 2 but utilizes differently shaped components of the lens body. Referring to FIG. 7, a first lens body portion 61 is a generally U-shaped portion attached to a position-fixation member 62 similar to the position-fixation member 44 of FIGS. 2 and 3. Referring to FIG. 6, a second lens body portion 63 is insertable into the first lens body portion within the eye and includes a curved lens body portion 63c extending to a position-fixation member 64 similar in the position-fixation member 45 of FIGS. 2 and 4. The opening between the legs 61a, 61b of the lens body portion 61 of FIG. 7 may, for example, be of 2 mm width. The lens body portion 63 has a corresponding width so that after the lens portions individually represented in FIGS. 6 and 7 are inserted into the eye and the position-fixation members 62 and 64 are connected together to form the lens 60, two straight edge lines 66, 67 extend across substantially the width of the lens 60 but are displaced from the central focal region of the eye, thereby minimizing any interference in the primary region of vision.

By bending the legs 61a, 61b of the first lens body portion 61 of FIG. 7 toward each other to the extent where they partly overlap one another, the first lens body portion 61 of FIG. 7 can be deformed to a smaller dimension than when undeformed, for insertion through the opening in the eye. The opening in the eye need, therefore, be only slighly over 3 mm in length if the width of each of the legs 61a, 61b and of the lens body portion 63, is, for example, 2 mm. Locking pin 68 on the lens body portion 63 may be inserted in the opening 69 of the body portion 61 to lock the lens body portions together. The position-fixation members 62 and 64 are connected by the surgeon within the eye in a manner similar to the position-fixation members 44, 45 of the lens of FIGS. 1 and 2.

Referring now to FIGS. 9, 10 and 11, a plurality of lens body portions 70, 71 which are separable outside an eye are there represented. A plurality of position-fixation members 73, 74 extend from curved portions 70d, 70c of the lens body portion 70. The position-fixation members 73, 74 are shaped similarly to the position-fixation members 40, 42 of FIG. 2, but, of course, are not constructed to be connectable with each other since they extend from the same lens body portion 70b. In the example shown, the lens body portion 71 has a larger width dimension than the lens body portion 70.

The lens body portion 70 and the position-fixation members 73, 74 may be inserted into the eye through an opening slightly larger than the width of the lens body portion 71 by snaking through the opening in the eye the position-fixation member 73, the curved body portion 70d, the body portion 70b, the curved body portion 70c and the position-fixation member 74. The lens body portion 70 and position-fixation members 73, 74 may be held in position by the surgeon using a second instrument through another opening in the eye usually made for other purposes.

The lens body portion 71 may then be inserted through the same opening in the eye as the lens body portion 70. The lens includes means for locking together the lens body portions 70, 71 comprising pins 72 extending from the lens body portion 71 and apertures 75 for receiving the pins in the lens body portion 70. The curved body portions 70c and 70d may be deformed by the surgeon while he inserts the pins 72 into the apertures 75. The lens body portions 70, 71 and the position-fixation members 73, 74 may then be positioned and seated in the eye.

Referring now to FIG. 12, a plurality of lens body portions 80, 81 which are separable outside an eye are there represented. These body portions, when assembled by abutting each other along diametral surfaces 80a, 81a, form a circular optic. A plurality of position-fixation members 83, 84 extend from the lens body portions 80, 81, respectively. The position-fixation members 84, 84 are preferably in the form of resilient, i.e. springy members.

The lens body portion 80 and the position-fixation member 83, may be inserted into the eye through an opening only slightly larger than the width of the lens body portion 80 by snaking the position-fixation member 83 through the opening in the eye and inserting the lens body portion 80 through the opening in the eye in a direction substantially parallel to surface 80a. The lens body portion 80 and position-fixation member 83 may be held in position in the eye by the surgeon using a second instrument through another opening in the eye usually made for other purposes.

The lens body portion 81 may then be inserted in a similar manner through the same opening in the eye as the lens body portion 80. The lens includes means for locking together the lens body portions 80, 81 comprising pins 82 extending from the lens body portion 80 and apertures 85 in the lens body portion 81 for receiving the pins 82 with a friction fit. After both body portions 80, 81 have been separately inserted into the eye, the surgeon may assemble these parts together inside the eye by inserting the pins 82 into the apertures 85. The lens body portions 80, 81 and the position-fixation members 83, 84 may then be positioned and seated in the eye.

The lens body portions 80, 81 may also be formed with their abutting surfaces 80a, 81a removed by, for example, 1 mm from the optical axis of the optic.

The assembled lens preferably is of the type which will fit the range of anterior chamber diameter sizes most commonly exhibited by human eyes while limiting movement of the optic in anterior direction toward the cornea to a position in which the optic will be sufficiently spaced from the cornea to minimize risk of contact between the optic and the cornea during normal deformations of the eyeball, as described and claimed in my copending application Ser. No. 247,570, filed Mar. 25, 1981, now U.S. Pat. No. 4,370,760.

From the foregoing description it will be apparent that an intraocular lens constructed in accordance with the invention has the advantage that the lens can be inserted into the eye through an opening which is smaller than the diameter of the lens body or optic.

While there have been described what are at present considered to be the preferred embodiments of this invention, it will be obvious to those skilled in the art that various changes and modifications may be made therein without departing from the invention, and it is, therefore, aimed to cover all such changes and modifications as fall within the true spirit and scope of the invention.

What is claimed is:

1. An intraocular lens comprising:
   a lens body having a plurality of portion which are separable outside an eye;
   a plurality of position-fixation members extending from said lens body for fixating the position of said lens body portions within the eye;

a plurality of lens portions comprising said lens body portions and said position-fixation members, said plurality of lens portions being individually insertable through an opening in the eye and being connectable within the eye to form the lens.

2. A lens in accordance with claim 1 in which said plurality of portions of said lens body is two portions.

3. A lens in accordance with claim 1 in which said plurality of lens portions comprises:

a first lens portion comprising a first of said lens body portions and a first of said position-fixation members extending therefrom; and a second lens portion comprising a second of said lens body portions and a second of said position-fixation members extending therefrom.

4. A lens in accordance with claim 3 in which said first and second position-fixation members are connectable within the eye.

5. A lens in accordance with claim 3 in which said first position-fixation member extends tangentially from said first lens body portion.

6. A lens in accordance with claim 3 in which said second body portion includes a curved peripheral portion from which said second position-fixation member extends.

7. A lens in accordance with claim 3 in which said second position-fixation member has a hollow longitudinally extending portion and in which said first position-fixation member has a longitudinally extending portion insertable into said hollow longitudinally extending portion within the eye.

8. A lens in accordance with claim 3 in which each of said first and second position-fixation members has a stem portion and a limb portion extending therefrom, each limb portion having two regions adapted for contact with the eye.

9. A lens in accordance with claim 3 in which said lens body has a circular periphery and in which said first and second lens portions can be so connected within the eye that said first and second lens body portions abut each other along a diameter of said lens body.

10. A lens in accordance with claim 3 in which said lens body has a circular periphery and in which said first and second lens portions can be so connected within the eye that said first and second lens body portions abut each other along a line displaced from a diameter of said lens body.

11. A lens in accordance with claim 3 in which said first lens body portion is a generally U-shaped portion.

12. A lens in accordance with claim 11 in which said second lens body portion is insertable into said first lens body portion within the eye.

13. A lens in accordance with claim 11 in which said first lens body portion can be deformed to a smaller dimension, than when undeformed, for insertion through the opening in the eye.

14. A lens in accordance with claim 3 which includes means for locking together said first and second body portions after insertion thereof into the eye.

15. A lens in accordance with claim 1 in which said plurality of position-fixation members extend from one of said lens body portions.

16. A lens in accordance with claim 2 in which two position-fixation members extend from one of said lens body portions.

17. A lens in accordance with claim 1 or claim 16 which includes means for locking together said lens body portions.

18. A lens in accordance with claim 17 in which said means for locking together said lens body portions comprises pins extending from one of said lens body portions and apertures for receiving said pins in another of said lens body portions.

19. A method of positioning in an eye an intraocular lens having a plurality of lens portions which are separable outside the eye, the lens portions including lens body portions and position-fixation members, the lens portions being connectable, comprising:

inserting a first lens body portion and at least one position-fixation member through an opening in the eye;

inserting a second lens body portion through the opening in the eye; and connecting said lens portions inside the eye to position said lens body portions and said position-fixation members in the eye.

20. A method in accordance with claim 19 in which each of said lens portions includes a lens body portion and a position-fixation member extending therefrom, the position-fixation members being connectable, in which the step of inserting a first body portion and at least one position-fixation member through the opening in the eye comprises inserting said first body portion and one position-fixation member through the opening in the eye, in which the step of inserting a second lens body portion through the opening in the eye comprises inserting said second lens body portion and a second position-fixation member through the opening in the eye, and in which the step of connecting said lens portions inside the eye comprises connecting said first and second position-fixation members inside the eye.

21. A method in accordance with claim 20 in which the steps of inserting said lens body portions and said position-fixation members through an opening in the eye comprise snaking the individual lens body portions and position-fixation members through the opening in the eye.

22. A method in accordane with claim 20 in which one of said position-fixation members has a hollow longitudinally extending portion and another of said position-fixation members has a longitudinally extending portion insertable therein and in which the step of connecting said first and second position-fixation members comprises inserting said longitudinally extending portion of said other position-fixation member into said hollow longitudinally extending portion of said one position-fixation member.

23. A method in accordance with claim 19 in which one lens portion includes a lens body portion and two position-fixation members extending therefrom and another lens body portion includes means cooperative with said one lens body portion for locking together said lens body portions, in which the step of inserting a first lens body portion and at least one position-fixation member through an opening in the eye comprises the step of inserting said first lens body portion and said two position-fixation members through the opening in the eye, and in which the step of connecting said lens portions inside the eye comprises utilizing said means cooperative with said one lens body portion for locking together said lens body portions.

* * * * *